(12) United States Patent
Streckfus (10) Patent No.: US 11,078,256 B2
(45) Date of Patent: Aug. 3, 2021

(54) METHODS AND COMPOSITIONS FOR INHIBITING CANCER CELL GROWTH

(71) Applicant: THE BOARD OF REGENTS OF THE UNIVERSITY OF TEXAS SYSTEM, Austin, TX (US)

(72) Inventor: Charles F. Streckfus, Houston, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 16/452,178

(22) Filed: Jun. 25, 2019

(65) Prior Publication Data

US 2019/0389938 A1     Dec. 26, 2019

Related U.S. Application Data

(60) Provisional application No. 62/690,034, filed on Jun. 26, 2018.

(51) Int. Cl.
    *C07K 14/81*      (2006.01)
    *A61K 9/19*      (2006.01)
    *A61K 9/00*      (2006.01)

(52) U.S. Cl.
    CPC ........ *C07K 14/8146* (2013.01); *A61K 9/0019* (2013.01); *A61K 9/19* (2013.01)

(58) Field of Classification Search
    CPC ............................... C07K 14/8146; A61K 9/19
    See application file for complete search history.

(56) References Cited

U.S. PATENT DOCUMENTS

| | | | |
|---|---|---|---|
| 6,294,349 B1 | 9/2001 | Streckfus et al. | |
| 6,972,180 B1 | 12/2005 | Streckfus et al. | |
| 8,772,038 B2 | 7/2014 | Streckfus et al. | |
| 2010/0279419 A1* | 11/2010 | Streckfus | G01N 27/62 436/64 |
| 2013/0116343 A1* | 5/2013 | Streckfus | G01N 33/6893 514/789 |
| 2013/0280743 A1* | 10/2013 | Streckfus | G01N 27/62 435/23 |

FOREIGN PATENT DOCUMENTS

JP     2012-232923    * 11/2012    ............ C07K 14/47

OTHER PUBLICATIONS

Streckfus et al., 2017, Salivary proline rich peptide decreases cell growth in HCC38 triple negative breast cancer cell line, Journal of Solid Tumors, 7(2): 38-44.*
Streckfus et al., 2000, The Presence of Soluble c-erbB-2 in Saliva and Serum among Women with Breast Carcinoma: A Preliminary Study, Clinical Cancer Research, 6: 2363-2370.*
Streckfus et al., 2009, A Comparison of the Proteomic Expression in Pooled Saliva Specimens from Individuals Diagnosed with Ductal Carcinoma of the Breast with and without Lymph Node Involvement, Journal of Oncology, 11 pages.*
Streckfus et al., 2016, A Catalogue of Altered Salivary Proteins Secondary to Invasive Ductal Carcinoma: A Novel In Vivo Paradigm to Assess Breast Cancer Progression, Scientific Reports, 6: 30800, 18 pages.*
Streckfus et al., 2008, Breast Cancer Related Proteins Are Present in Saliva and Are Modulated Secondary to Ductal Carcinoma In Situ of the Breast, Cancer Investigation, 26(2): 159-167.*
Streckfus et al., 2012, Salivary Protein Profiles among HER2/neu-Receptor-Positive and -Negative Breast Cancer Patients: Support for Using Salivary Protein Profiles for Modeling Breast Cancer Progression, Journal of Oncology, 9 pages.*
Koffler, Jennifer, et al. "Submaxillary gland androgen-regulated protein 3A expression is an unfavorable risk factor for the survival of oropharyngeal squamous cell carcinoma patients after surgery." *European Archives of Oto-Rhino-Laryngology* 270.4 (2013): 1493-1500.
Streckfus, Charles F., and Lenora Bigler. "A catalogue of altered salivary proteins secondary to invasive ductal carcinoma: a novel in vivo paradigm to assess breast cancer progression." *Scientific Reports* 6.1 (2016): 1-18.

* cited by examiner

*Primary Examiner* — Amber D Steele
(74) *Attorney, Agent, or Firm* — Parker Highlander PLLC (57) ABSTRACT

Described are methods and compositions that provide for generating synthetic or recombinant proline rich peptides. In some aspects, p1978 compositions are used to inhibit breast cancer cell growth and thus provided is a method for treating and preventing breast cancer cell growth in a mammal.

10 Claims, 4 Drawing Sheets
Specification includes a Sequence Listing.

Figure 1. Experimental design schematic.

Figure 2. Bar graph exhibiting mean cell line values with standard deviations for 8.26 ug/ml of p1978.

Figure 3. Bar graph exhibiting mean cell line values with standard deviations for 16.52 ug/ml of p1978.

Figure 4. Possible inhibition of Ras pathway by p1978.

Figure 5A- p1978 amino acid sequence – SEQ ID NO: 1

PRGPYPPGPLAPPQ

Figure 5B - p1978 sequence of most likely codons – SEQ ID NO: 2 ccg cgc ggc ccg tat ccg ccg ggc ccg ctg gcg ccg ccg cag

Figure 5C - consensus codons –SEQ ID NO: 3 ccn mgn ggn ccn tay ccn ccn ggn ccn ytn gcn ccn ccn car

SEQUENCE LISTING

<160> NUMBER OF SEQ ID NOS: 4

<210> SEQ ID NO 1
<211> LENGTH: 14
<212> TYPE: PRT
<213> ORGANISM: Artificial sequence
<220> FEATURE:
<223> OTHER INFORMATION: Synthetic amino acid

<400> SEQUENCE: 1

Pro Arg Gly Pro Tyr Pro Pro Gly Pro Leu Ala Pro Pro Gln
1               5                   10

<210> SEQ ID NO 2
<211> LENGTH: 42
<212> TYPE: DNA
<213> ORGANISM: Artificial sequence
<220> FEATURE:
<223> OTHER INFORMATION: Synthetic oligonucleotide

<400> SEQUENCE: 2
ccgcgcggcc cgtatccgcc gggcccgctg gcgccgccgc ag                           42

<210> SEQ ID NO 3
<211> LENGTH: 42
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:

```
<221> NAME/KEY: misc_feature
<222> LOCATION: (39)..(39)
<223> OTHER INFORMATION: n is a, c, g, or t

<400> SEQUENCE: 3
ccnmgnggnc cntayccncc nggnccnytn gcnccnccnc ar                             42

<210> SEQ ID NO 4
<211> LENGTH: 79
<212> TYPE: PRT
<213> ORGANISM: Artificial sequence
<220> FEATURE:
<223> OTHER INFORMATION: Synthetic amino acid

<400> SEQUENCE: 4

Met Lys Ser Leu Thr Trp Ile Leu Gly Leu Trp Ala Leu Ala Ala Cys
1               5                   10                  15

Phe Thr Pro Gly Glu Ser Gln Arg Gly Pro Arg Gly Pro Tyr Pro Pro
                20                  25                  30

Gly Pro Leu Ala Pro Pro Gln Pro Phe Gly Pro Gly Phe Val Pro Pro
            35                  40                  45

Pro Pro Pro Pro Pro Tyr Gly Pro Gly Arg Ile Pro Pro Pro Pro Pro
        50                  55                  60

Ala Pro Tyr Gly Pro Gly Ile Phe Pro Pro Pro Pro Gln Pro
65                  70                  75
```

US 11,078,256 B2

METHODS AND COMPOSITIONS FOR INHIBITING CANCER CELL GROWTH

This application claims the benefit of U.S. Provisional Patent Application No. 62/690,034, filed Jun. 26, 2018, the entirety of which is incorporated herein by reference.

INCORPORATION OF SEQUENCE LISTING

The sequence listing that is contained in the file named "UTSHP0348US_updated_ST25.txt", which is 3 KB (as measured in Microsoft Windows®) and was created on Jan. 22, 2021, is filed herewith by electronic submission and is incorporated by reference herein.

TECHNICAL FIELD

Generally described herein are methods and compositions for the treatment of breast cancer in mammals.

BACKGROUND

Carcinoma of the breast is the second most common type of cancer among women primarily affecting the ductal and lobular tissues of the breast. The affliction constitutes a major public health burden.[1, 2] Despite improved early detection, diagnosis and aggressive treatment approaches, consisting of surgery, radiotherapy and/or chemotherapy, carcinoma of the breast is still a great threat to human life. [1, 2] Regardless of these advances, we still have an incomplete knowledge of the molecular principles underlying the malignant progression as well as the development and maintenance of local recurrence and distant metastasis of this cancer type. Additionally, there is also the problem in rendering treatment of triple negative breast carcinomas, which are more aggressive than other types of breast cancer and respond poorly to treatments such as hormonal and Her2/neu receptor therapy.

To date, there is a paucity of knowledge on the expression and function of opiorphin coding genes both in health and in particular, the pathogenesis and malignant progression of breast cancer. Consequently, the purpose of this study was to determine the effects, if any, on the growth triple negative breast cancer cell line by inoculating it with a proline rich peptide segment (p1978) from the parent SMR3B protein.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION

Definitions

In this disclosure, the use of the singular includes the plural, the word "a" or "an" means "at least one", and the use of "or" means "and/or", unless specifically stated otherwise. Furthermore, the use of the term "including", as well as other forms, such as "includes" and "included", is not limiting. Also, terms such as "element" or "component" encompass both elements and components comprising one unit and elements or components that comprise more than one unit unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated herein by reference in their entirety for any purpose. In the event that one or more of the incorporated literature and similar materials defines a term in a manner that contradicts the definition of that term in this application, this application controls.

As used herein, "patient" or "subject" includes mammalian organisms or tissue which are capable of undergoing surgical procedures, such as but not limited to skin, mucosa, tongue or muscle biopsy or tumor excision procedures, as described herein, such as human and non-human mammals, for example, but not limited to, rodents, mice, rats, non-human primates, companion animals such as dogs and cats as well as livestock, e.g., sheep, cow, horse, etc.

As used herein, and unless otherwise indicated, the terms "treat," "treating," "treatment" and "therapy" contemplate surgical and therapeutic medical procedures, such as but not limited to observing and monitoring the size of a lesion, biopsy of a lesion, excision of a lesion, and spatial orientation to direct therapies such as radiation or heat.

One salivary protein that has been repeatedly found up regulated among salivary proteomic analysis is the submaxillary gland androgen-regulated protein 3B (SMR3B; P02814). The SMR3B is an 8.188 kilodalton protein that belongs to the gene family whose other members are SMR3A and PROL1, which all produce opiorphin homologs.[5] Opiorphins are small peptides derived by post-translational processing from their parent proteins. Opiorphins have been identified as a novel class of peptides that act as potent endogenous mem-brane metalloendopeptidase inhibitors.

Embodiments of the present disclosure include the use of SMR3B derived proline rich peptides, such as, but, not limited to p1978 as an anti-tumor therapy. In some embodiments the peptides are synthetic or recombinant proline rich peptide segments of SMR3B. In certain aspects, the synthetic or recombinant proline rich peptide segment of SMR3B is that of p1978. The amino acid sequence of p1978 is PRGPYPPGPLAPPQ (SEQ ID NO: 1). In some embodiments a recombinant polypeptide comprising the p1978 amino acid coding sequence. In some embodiments, the polypeptide is a fusion protein comprising the p1978 coding sequence and a heterologous polypeptide sequence. In some embodiments, a synthetic polypeptide comprising a p1978 amino acid coding sequence. While in other embodiments are compositions comprising a peptide having the amino acid sequence p1978 and a pharmaceutically acceptable carrier. In some embodiments, this composition is frozen or lyophilized. In additional embodiments is an isolated polynucleotide molecule comprising a nucleic acid sequence encoding the polypeptide of p1978. In some aspects, the nucleic acid sequence encoding the polypeptide is operably linked to a promoter. And in other aspects this polynucleotide sequence is expressed by a host cell and thus in some embodiments is a host cell comprising a polynucleotide molecule comprising a nucleic acid sequence encoding the polypeptide of p1978. In additional embodiments is a method of manufacturing a recombinant polypeptide comprising: (a) expressing a polynucleotide molecule encoding the polypeptide of p19'78; and (b) purifying the polypeptide from the cell. Alternatively the polypeptide can be secreted from the cell. In some embodiments are methods of treating or preventing a breast cancer in a subject in need of such treatment, the treatment comprising administering an effective amount of a composition comprising the peptide p19'78, alone or in combination with known anti-breast cancer agents or therapies. In some embodiments the breast cancer is triple negative breast cancer. In some embodiments the composition comprising p1978 peptide is administered by intravenous injection or catheter delivery or through an alternative route of administration.

In additional embodiments are pharmaceutical compositions comprising proline rich peptide segments of SMR3B and in certain aspects these composition comprise the proline rich peptide of p1978. In a further embodiment, a method of treating or preventing a breast cancer in a subject is provided that comprises administering an effective amount of a p1978 composition comprising a recombinant or synthetic p1978 peptide, In some aspects, the breast cancer may be a triple negative breast cancer. In some aspects an effective amount of a p1978 composition provides cytotoxic or cytostatic activity that prevents tumor cell growth or induces tumor cell death. In accordance with certain embodiments, a method of treating or preventing breast cancer or a complication thereof in a mammal, is provided. Another embodiment provides a method of treating breast cancer in a mammal, which comprises delivery of an amount of p1978 composition to the mammal to stop the growth of tumor cells.

As demonstrated in the examples below, the p1978 peptide, in both high and low doses, inhibits cancer cell growth. With respect to the HCC38 cell lines, the overall effect appeared to remain the same with a few exceptions. When the concentration of p1978 increased, it yielded a corresponding increase in cell viability. Additionally, there was a decrease in the difference between the control and treatment groups cell counts. Growth rate decreased regardless of dosage; however, the lower dosage appeared to have a higher impact on the rate of cell growth. With respect to the 184B5 and AU565 cell lines, the low dose had minor effect on the 184B5 and AU565 cell lines; however, this was not the case when the dose was doubled.

Starting with the 184B5 cell line, doubling the concentration of p1978 produced several interesting findings. As exhibited in FIG. 2 and Table 2, the mean number of cells increased among the 184B5 cell lines. The treated cell lines became higher in cell counts than the control. This was in contrast to lower dose results where the treatment group produced cell counts below that of the control. The higher dose also increased cell viability from 91 to between 95 to 98 percent. The growth rates also increased with a higher p1978 concentration (see Table 3). The AU565 cell line exhibited a positive response to both dosages. The cell counts for the treated cells where higher than controls and the treated cells exhibited a higher growth rate when compared to its counterpart.

Figure 4:
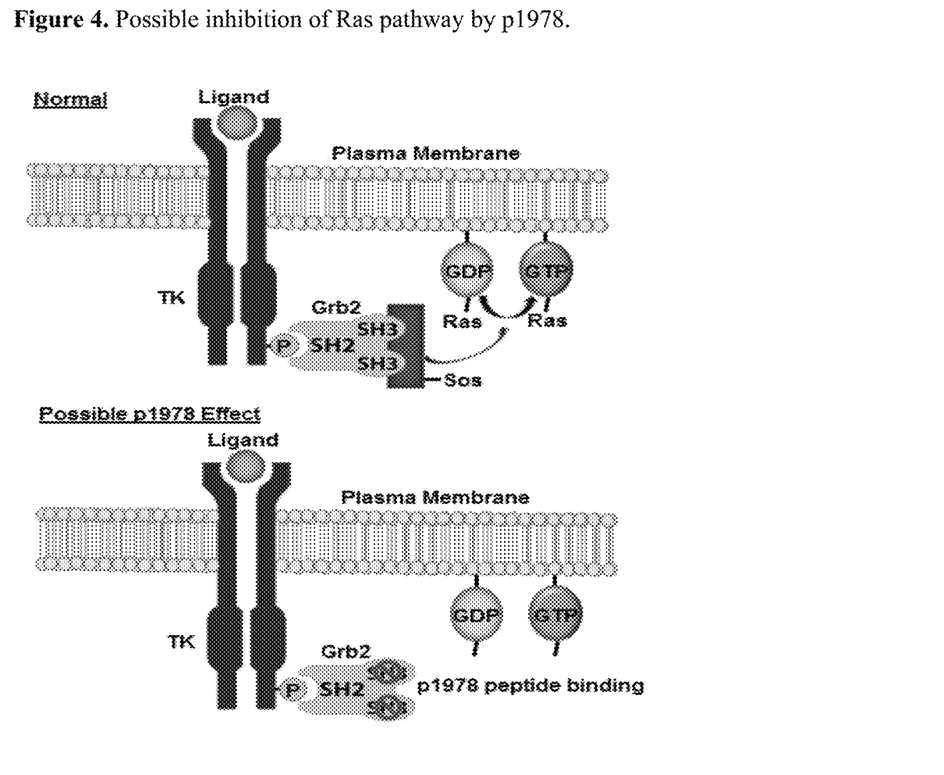
FIG. 4: Possible inhibition of Ras pathway by p1978.
Figure 5A:
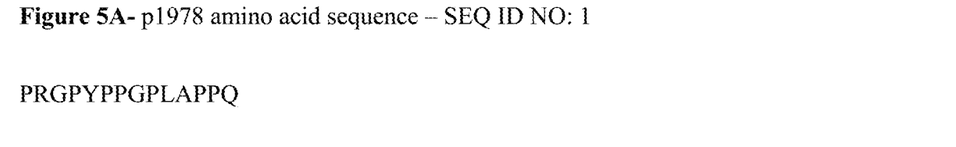
FIG. 5A: p1978 amino acid sequence—SEQ ID NO: 1
Figure 5B:
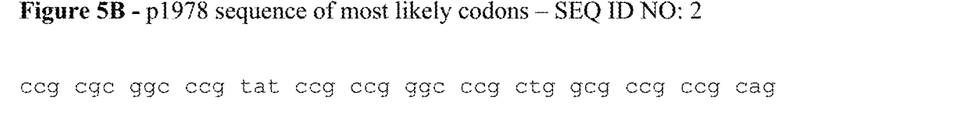
FIG. 5B: p1978 sequence of most likely codons—SEQ ID NO: 2
Figure 5C:
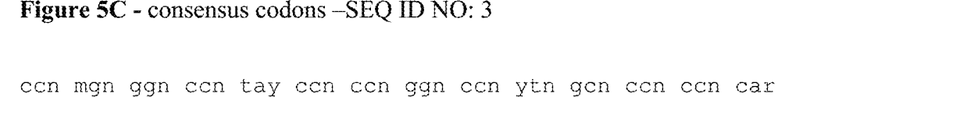
FIG. 5C: Consensus codons—SEQ ID NO: 3

One of the hallmarks of salivary proline rich peptides is their ability to cross cell membranes without damage and exploit intracellular activity [8]. This, may be the case with p1978. While the not wishing to limit the invention to any particular mechanism of action, once inside the cell, p1978 may interact with the SH3 as illustrated in FIG. 4, which diagrams its possible effects on the Ras pathway. As shown in FIG. 4, the pathway begins with a ligand activated growth factor receptor that produces a tyrosine kinase receptor response. Consequently, Grb2, an adaptor protein, interacts via its SH2 domain with the autophosphorylated carboxyl-terminal tail of the activated receptor and via the SH3 domains with proline-rich sequences found in the Ras guanine releasing factor (Sos). The cascade of events lead to Ras activation.[9-13] Grb2 has two SH3 domains that recognize the PxxP consensus sequence.[11] The PxxP sequence is also present in the p1978 peptide.[9-13] With this in mind, it may be that p1978 peptide has a higher affinity to the Grb2/SH3 domains thereby inhibiting Ras activation by blocking Sos binding to Grb2 in the HCC38 cell line (see FIG. 4). This in turn may reduce cellular proliferation. In conclusion, the examples demonstrate that there is a reduction of triple receptor negative breast cancer cell growth associated with proline rich peptides and in a specific embodiment the proline rich peptide of p1978

In additional aspects, proline rich peptide segments of SMR3B, such as p1978 may be further modified by one or more other amino substitutions while maintaining their biological activity. For example, amino acid substitutions can be made at one or more positions wherein the substitution is for an amino acid having a similar hydrophilicity. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Thus such conservative substitution can be made in GrB and will likely only have minor effects on their activity. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (0.5); histidine −0.5); cysteine (−1.0); methionine (−1.3); valine (−1.5); leucine (−1.8); isoleucine (−1.8); tyrosine (−2.3); phenylalanine (−2.5); tryptophan (−3.4). These values can be used as a guide and thus substitution of amino acids whose hydrophilicity values are within ±2 are preferred, those that are within ±1 are particularly preferred, and those within ±0.5 are even more particularly preferred. Thus, any of proline rich peptide segments of SMR3B, such as p1978 herein may be modified by the substitution of an amino acid, for different, but homologous amino acid with a similar hydrophilicity value. Amino acids with hydrophilicities within +/−1.0, or +/−0.5 points are considered homologous. Furthermore, it is envisioned that proline rich peptide segments of SMR3B, such as p1978 may be modified by amino acid deletions, substitutions, additions or insertions while retaining its biological activity.

Proline rich peptide segments of SMR3B, such as p1978 as well as fusion proteins in which the peptide is fused to an unrelated protein are also within the scope of the invention and can be designed on the basis of the proline rich peptide nucleotide and amino acid sequences. Such fusion proteins include but are not limited to IgFc fusions which stabilize the proline rich peptide and prolong half-life in vivo or in in vitro assays; fusions to any amino acid sequence that allows the fusion protein to be anchored to the cell membrane; or fusions to an enzyme, fluorescent protein, or luminescent protein which provide a marker function.

While proline rich peptide can be chemically synthesized (e.g., see Creighton, 1983), proline rich peptides, such as p1978, may advantageously be produced by recombinant DNA technology using techniques well known in the art for expressing nucleic acids. Such methods can be used to construct expression vectors containing the proline rich peptides, such as p1978 nucleotide sequences and appropriate transcriptional and translational control signals. These methods include, for example, in vitro recombinant DNA techniques, synthetic techniques, and in vivo genetic recombination. See, for example, the techniques described in Sambrook et al., 1989, supra, and Ausubel et al., 1989, supra. Alternatively, RNA capable of encoding proline rich peptides, such as p1978 nucleotide sequences may be chemically synthesized using, for example, synthesizers. See, for example, the techniques described in "Oligonucleotide Synthesis", 1984, Gait, M. J., ed., IRL Press, Oxford, which is incorporated by reference herein in its entirety.

A variety of host-expression vector systems can be utilized to express the p1978 nucleotide sequences of embodiments of the invention. Where p1978 polypeptide is a soluble derivative (e.g., with a deleted TMD), the polypeptide can be recovered from the culture, i.e., from the host cell in cases where p1978 polypeptide is not secreted, and from the culture media in cases where p1978 polypeptide is secreted by the cells. However, the expression systems also encompass engineered host cells that express p1978 or functional equivalents in situ, i.e., anchored in the cell membrane. Purification or enrichment of p1978 from such expression systems can be accomplished using appropriate detergents and lipid micelles and methods well known to those skilled in the art. However, such engineered host cells themselves can be used in situations where it is important not only to retain the structural and functional characteristics of p19'78, but to assess biological activity, e.g., in drug screening assays.

For long-term, high-yield production of recombinant proteins, stable expression is preferred. For example, cell lines which stably express p1978 sequences can be engineered. Rather than using expression vectors which contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the P1978 gene product. Such engineered cell lines may be particularly useful in screening and evaluation of compounds that affect the endogenous activity of the P1978 gene product. A number of selection systems can be used, including but not limited to the herpes simplex virus thymidine kinase (Wigler, et al., 1977), hypoxanthine-guanine phosphoribosyltransferase (Szybalska & Szybalski, 1962), and adenine phosphoribosyltransferase (Lowy, et al., 1980) genes can be employed in tk-, hgprt- or aprt-cells, respectively. Also, anti-metabolite resistance can be used as the basis of selection for the following genes: dhfr, which confers resistance to methotrexate (Wigler, et al., 1980; O'Hare, et al., 1981); gpt, which confers resistance to mycophenolic acid (Mulligan & Berg, 1981); neo, which confers resistance to the aminoglycoside G-418 (Colberre-Garapin, et al., 1981); and hygro, which confers resistance to hygromycin (Santerre, et al., 1984).

The expression systems that can be used for purposes of the embodiments include but are not limited to microorganisms such as bacteria (e.g., *E. coli, B. subtilis*) transformed with recombinant bacteriophage DNA, plasmid DNA or cosmid DNA expression vectors containing p1978 nucleotide sequences; yeast (e.g., *Saccharomyces, Pichia*) transformed with recombinant yeast expression vectors containing the p1978 nucleotide sequences; insect cell systems infected with recombinant virus expression vectors (e.g., baculovirus) containing the p1978 sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing P1978 nucleotide sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the p1978 gene product being expressed. For example, when a large quantity of such a protein is to be produced, for the generation of pharmaceutical compositions of p1978 protein or for raising antibodies to the p1978 protein, for example, vectors which direct the expression of high levels of fusion protein products that are readily purified may be desirable. Such vectors include, but are not limited, to the *E. coli* expression vector pUR278 (Ruther et al., 1983), in which the p1978 coding sequence may be ligated individually into the vector in frame with the lacZ coding region so that a fusion protein is produced; pIN vectors (Inouye & Inouye, 1985; Van Heeke & Schuster, 1989); and the like. pGEX vectors may also be used to express foreign polypeptides as fusion proteins with glutathione S-transferase (GST). In general; such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhidrosis virus (AcNPV) is used as a vector to express foreign sequences. The virus grows in *Spodoptera frugiperda* cells. The p1978 gene coding sequence may be cloned individually into non-essential regions (for example the polyhedrin gene) of the virus and placed under control of an AcNPV promoter (for example the polyhedrin promoter). Successful insertion of p1978 coding sequence will result in inactivation of the polyhedrin gene and production of non-occluded recombinant virus, (i.e., virus lacking the proteinaceous coat coded for by the polyhedrin gene). These recombinant viruses are then used to infect *Spodoptera frugiperda* cells in which the inserted polynucleotide is expressed (e.g., see Smith et al., 1983 and U.S. Pat. No. 4,215,051).

In mammalian host cells, a number of viral-based expression systems can be utilized. In cases where an adenovirus is used as an expression vector, the p1978 nucleotide sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the p1978 gene product in infected hosts (e.g., See Logan & Shenk, 1984). Specific initiation signals may also be important for efficient translation of inserted p1978 nucleotide sequences. These signals include the ATG initiation codon and adjacent sequences. In cases where an entire p1978 gene or cDNA, including its own initiation codon and adjacent sequences, is inserted into the appropriate expression vector, no additional translational control signals may be needed. However, in cases where only a portion of the p1978 coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (See Bitter, et al., 1987).

In yeast, a number of vectors containing constitutive or inducible promoters may be used. For a review, see Current Protocols in Molecular Biology, 1988; Grant, et al., 1987; Wu & Grossman, 1987; Bitter, 1987; and "The Molecular Biology of the Yeast *Saccharomyces*", 1982.

In cases where plant expression vectors are used, the expression of the coding sequence may be driven by any of a number of promoters. For example, viral promoters such as the 35S RNA and 19S RNA promoters of CaMV (Brisson et al., 1984), or the coat protein promoter of TMV (Takamatsu et al., 1987) may be used; alternatively, plant promoters such as the small subunit of RUBISCO (Coruzzi et al., 1984; Broglie et al., 1984); or heat shock promoters, e.g., soybean hsp17.5-E or hsp17.3-B (Gurley et al., 1986) may be used. These constructs can be introduced into plant cells using Ti plasmids, Ri plasmids, plant virus vectors, direct DNA transformation, microinjection, electroporation, etc. For reviews of such techniques see, for example, Methods for Plant Molecular Biology 1988; and Grierson & Corey, 1988.

A variety of host-expression vector systems can be utilized to express the p1978 nucleotide sequences of embodiments of the invention. Where p1978 polypeptide is a soluble derivative (e.g., with a deleted TMD), the polypeptide can be recovered from the culture, i.e., from the host cell in cases where p1978 polypeptide is not secreted, and from the culture media in cases where p1978 polypeptide is secreted by the cells. However, the expression systems also encompass engineered host cells that express p1978 or functional equivalents in situ, i.e., anchored in the cell membrane. Purification or enrichment of p1978 from such expression systems can be accomplished using appropriate detergents and lipid micelles and methods well known to those skilled in the art. However, such engineered host cells themselves can be used in situations where it is important not only to retain the structural and functional characteristics of p19'78, but to assess biological activity, e.g., in drug screening assays.

For long-term, high-yield production of recombinant proteins, stable expression is preferred. For example, cell lines which stably express p1978 sequences can be engineered, for example, as described in the examples below. Rather than using expression vectors which contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the P1978 gene product. Such engineered cell lines may be particularly useful in screening and evaluation of compounds that affect the endogenous activity of the P1978 gene product. A number of selection systems can be used, including but not limited to the herpes simplex virus thymidine kinase (Wigler, et al., 1977), hypoxanthine-guanine phosphoribosyltransferase (Szybalska & Szybalski, 1962), and adenine phosphoribosyltransferase (Lowy, et al., 1980) genes can be employed in tk-, hgprt- or aprt-cells, respectively. Also, anti-metabolite resistance can be used as the basis of selection for the following genes: dhfr, which confers resistance to methotrexate (Wigler, et al., 1980; O'Hare, et al., 1981); gpt, which confers resistance to mycophenolic acid (Mulligan & Berg, 1981); neo, which confers resistance to the aminoglycoside G-418 (Colberre-Garapin, et al., 1981); and hygro, which confers resistance to hygromycin (Santerre, et al., 1984).

The expression systems that can be used for purposes of the embodiments include but are not limited to microorganisms such as bacteria (e.g., *E. coli, B. subtilis*) transformed with recombinant bacteriophage DNA, plasmid DNA or cosmid DNA expression vectors containing p1978 nucleotide sequences; yeast (e.g., *Saccharomyces, Pichia*) transformed with recombinant yeast expression vectors containing the p1978 nucleotide sequences; insect cell systems infected with recombinant virus expression vectors (e.g., baculovirus) containing the P1978 sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing P1978 nucleotide sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the p1978 gene product being expressed. For example, when a large quantity of such a protein is to be produced, for the generation of pharmaceutical compositions of p1978 protein or for raising antibodies to the p1978 protein, for example, vectors which direct the expression of high levels of fusion protein products that are readily purified may be desirable. Such vectors include, but are not limited to, the *E. coli* expression vector pUR278 (Ruther et al., 1983), in which the p1978 coding sequence may be ligated individually into the vector in frame with the lacZ coding region so that a fusion protein is produced; pIN vectors (Inouye & Inouye, 1985; Van Heeke & Schuster, 1989); and the like. pGEX vectors may also be used to express foreign polypeptides as fusion proteins with glutathione S-transferase (GST). In general; such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhidrosis virus (AcNPV) is used as a vector to express foreign sequences. The virus grows in *Spodoptera frugiperda* cells. The p1978 gene coding sequence may be cloned individually into non-essential regions (for example the polyhedrin gene) of the virus and placed under control of an AcNPV promoter (for example the polyhedrin promoter). Successful insertion of p1978 coding sequence will result in inactivation of the polyhedrin gene and production of non-occluded recombinant virus, (i.e., virus lacking the proteinaceous coat coded for by the polyhedrin gene). These recombinant viruses are then used to infect *Spodoptera frugiperda* cells in which the inserted polynucleotide is expressed (e.g., see Smith et al., 1983 and U.S. Pat. No. 4,215,051).

In mammalian host cells, a number of viral-based expression systems can be utilized. In cases where an adenovirus is used as an expression vector, the p1978 nucleotide sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the p1978 gene product in infected hosts (e.g., See Logan & Shenk, 1984). Specific initiation signals may also be important for efficient translation of inserted p1978 nucleotide sequences. These signals include the ATG initiation codon and adjacent sequences. In cases where an entire p1978 gene or cDNA, including its own initiation codon and adjacent sequences, is inserted into the appropriate expression vector, no additional translational control signals may be needed. However, in cases where only a portion of the p1978 coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (See Bitter, et al., 1987).

In yeast, a number of vectors containing constitutive or inducible promoters may be used. For a review, see Current Protocols in Molecular Biology, 1988; Grant, et al., 1987; Wu & Grossman, 1987; Bitter, 1987; and "The Molecular Biology of the Yeast *Saccharomyces*", 1982.

In cases where plant expression vectors are used, the expression of the coding sequence may be driven by any of a number of promoters. For example, viral promoters such as the 35S RNA and 19S RNA promoters of CaMV (Brisson et al., 1984), or the coat protein promoter of TMV (Takamatsu et al., 1987) may be used; alternatively, plant promoters such as the small subunit of RUBISCO (Coruzzi et al., 1984; Broglie et al., 1984); or heat shock promoters, e.g., soybean hsp17.5-E or hsp17.3-B (Gurley et al., 1986) may be used. These constructs can be introduced into plant cells using Ti plasmids, Ri plasmids, plant virus vectors, direct DNA transformation, microinjection, electroporation, etc. For reviews of such techniques see, for example, Methods for Plant Molecular Biology 1988; and Grierson & Corey, 1988.

Therapeutic Formulation and Administration: Therapeutics comprising pharmaceutical compositions comprising proline rich peptide segments of SMR3B, such as p1978 and/or nucleic acids encoding proline rich peptides, such as p19'78, can be administered to a patient at therapeutically effective doses of pharmaceutical preparations used to treat or ameliorate conditions such as, but not limited to, breast cancers including but not limited to triple negative breast cancers. In various aspects, an effective amount of a proline rich peptides, such as p1978 composition may be an amount effective to inhibit tumor cell growth. In some aspects an effective amount of a proline rich peptides, such as p1978 composition provides enhancement or promotion of cytotoxic or cytostatic factors that inhibit tumor cell growth or induce tumor cell death. In further aspects a therapeutically effective dose refers to that amount of the composition sufficient to result in any amelioration or retardation of disease symptoms or progression in a mammal with breast cancer, to prevent and treat breast cancer. In further aspects, a proline rich peptides, such as p1978 composition can be used to prevent or treat breast cancer.

Toxicity and therapeutic efficacy of such proline rich peptide (such as p19'78) compositions can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compositions which exhibit large therapeutic indices are preferred. While compositions that exhibit toxic side effects may be used, care should be taken to design a delivery system that targets such compounds to the site of affected tissue in order to minimize potential damage to uninfected cells and, thereby, reduce side effects.

Data obtained from the cell culture assays and animal studies can be used in formulating a range of dosage for use in humans. The dosage of such compositions are preferably within a range of circulating concentrations that include the ED50 with little or no toxicity. The dosage may vary within this range depending upon the dosage form employed and the route of administration utilized. For any compositions used in the methods of the embodiments, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

When the therapeutic treatment of disease is contemplated, the appropriate dosage can also be determined using animal studies to determine the maximal tolerable dose, or MTD, of a bioactive agent per kilogram weight of the test subject. In general, at least one animal species tested is mammalian. Those skilled in the art regularly extrapolate doses for efficacy and avoiding toxicity to other species, including human. Before human studies of efficacy are undertaken, Phase I clinical studies in normal subjects help establish safe doses.

Additionally, the bioactive agent (e.g., a proline rich peptides, such as p1978) may be complexed with a variety of well-established compounds or structures that, for instance, enhance the stability of the bioactive agent, or otherwise enhance its pharmacological properties (e.g., increase in vivo half-life, reduce toxicity, etc.).

Pharmaceutical compositions for use in accordance with the present embodiments can be formulated in conventional manner using one or more physiologically acceptable carriers or excipients.

The above therapeutic compositions will be administered by any number of methods known to those of ordinary skill in the art including, but not limited to, administration by inhalation; by subcutaneous (sub-q), intravenous (I.V.), intraperitoneal (I.P.), intramuscular (I.M.), or intrathecal injection; or as a topically applied agent (transderm, ointments, creams, salves, eye drops, and the like). Thus, the compositions can be formulated for administration by inhalation or insufflation (either through the mouth or the nose) or oral, buccal, parenteral or rectal administration.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets can be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate. Preparations for oral administration can be suitably formulated to give controlled release of the active composition.

For buccal administration the compositions can take the form of tablets or lozenges formulated in conventional manner.

For administration by inhalation, the compositions for use according to the embodiments are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compositions can be formulated for parenteral administration by injection, e.g., by bolus injection or continuous infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compositions can also be formulated for rectal administration such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt. The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

Diagnostic use of peptide p1978: In some embodiments monitoring for p1978 can be used as an indicator of the possible presence of a cancer, and in particular a breast cancer. The presence of increased p1978 might also be used to as a companion assay to monitor the efficacy of a breast cancer therapeutic. In a previous proteomic studies by the inventor, LC-MS/MS analysis of saliva the proline rich protein SMR3B was found to be up-regulated in saliva secondary to carcinoma of the breast in situ [7]. In some embodiments, p1978 may be conjugated to create a fusion protein. In some embodiments the presence of p1978 can be detected using immunoassays and non-immunoassays for p1798, which will typically comprise incubating a sample, such as a biological fluid (such as saliva), a tissue extract, freshly harvested cells, or lysates of cells that have been incubated in cell culture, in the presence of a detectably labeled antibody capable of identifying p1978 or additional fragments of SMR3B and detecting the bound antibody by any of a number of techniques well-known in the art. The biological sample may be brought in contact with and immobilized onto a solid phase support or carrier such as nitrocellulose, or other solid support that is capable of immobilizing cells, cell particles, or soluble proteins. The support may then be washed with suitable buffers, followed by treatment with the detectably labeled antibody or fusion peptide. The solid phase support may then be washed with the buffer a second time to remove unbound antibody or fusion protein. The amount of bound label on solid support may then be detected by conventional means. The terms "solid phase support" or "carrier" are intended to include any support or carrier capable of binding an antigen or an antibody.

With respect to antibodies, one of the ways in which an antibody may be detectably labeled is by linking the same to an enzyme for use in an enzyme immunoassay (see, e.g., "Immunoassays: A Practical Approach" (Gosling, ed., Oxford University Press, Oxford, United Kingdom, 2000)). The enzyme that is bound to the peptide will react with an appropriate substrate, The detection may be accomplished by colorimetric methods that employ a chromogenic substrate for the enzyme; methods that employ a fluorogenic substrate in an enzyme-lined fluorescence (ELF) assay or by visual comparison of the extent of enzymatic reaction of a substrate in comparison with similarly prepared standards. A peptide or antibody also may be detectably labeled by coupling it to a chemiluminescent compound. The presence of the chemiluminescent-tagged peptide or antibody is detected by luminescence that arises during the course of a chemical reaction (see, e.g., U.S. Pat. Nos. 5,491,084, 5,625,048, 5,777,079, 5,795,737, 5,804,387, 5,874,304, 5,968,750, 5,976,796, 6,020,192, 6,027,881, 6,054,321, 6,096,865, 6,146,826, 6,172,188 and 6,265,548).

Immunochromatographic assays, also called lateral flow tests or simply strip tests, are a logical extension of the technology used in latex agglutination tests, the first of which was developed in 1956 by Singer and Plotz (Singer J. M. and Plotz C. M. The latex fixation test. I. Application to the serologic diagnosis of rheumatoid arthritis. Am. J. Med. 21, 888, 1956). The benefits of immunochromatographic tests include: their user-friendly format, short time to get test result, long-term stability over a wide range of climates and they are relatively inexpensive to make. These features make strip tests ideal for applications such as home testing, rapid point of care testing, and testing in the field, in places such as but not limited to the battlefield. In addition, they provide reliable testing that might not otherwise be available to rural environments or third world countries. Thus, such a format would have particular applicability in some cases by facilitating assessment of p1978 levels at home or at a dentist's, physician's or veterinarian's office or other medical facility.

The principle behind the test is straightforward, any ligand that can be bound to a visually detectable solid support, such as dyed microspheres, may be tested for qualitatively, and in many cases even semi-quantitatively. Some of the more common lateral flow tests currently on the market are tests for pregnancy, Strep throat, and *Chlamydia*. The two predominant approaches to lateral flow tests are the non-competitive (or direct) and competitive (or competitive inhibition) reaction format. The non-competitive (or direct) double antibody sandwich reaction format is used when testing for larger analytes with multiple antigenic sites, such as, for example, LH, hCG, and HIV. In this format, less than an excess of sample analyte is desired, so that some of the microspheres will not be captured at the capture line, and will continue to flow toward the second line of immobilized antibodies, the control line. This is usually a species-specific anti-immunoglobulin antibodies, specific for the conjugate antibodies on the microspheres. The competitive reaction format is used most often when testing for small molecules with single antigenic determinants, which cannot bind to two antibodies simultaneously. If this format is chosen, it is important to pay close attention to the amount of antibody bound to the microspheres, in relation to the amount of free antigen in the sample. If the sample does not contain an excess of free antigen, some of the microspheres will bind at the capture line, giving a weak signal, and making the test result ambiguous. Typically, the membranes used to hold the antibodies in place are made up of primarily hydrophobic materials. Both the microspheres used as the solid phase supports and the conjugate antibodies are hydrophobic, and their interaction with the membrane allows them to be effectively dried onto the membrane.

One variation of the above reaction formats avoids the problem of protein-coated microspheres sticking to the membrane non-specifically by using a membrane that is inert and does not bind antibodies. This makes migration of the mobile phase antibodies very efficient and reliable. The capture antibodies, rather than being physically bound by the membrane, are attached to large microspheres, which will be held in place physically, rather than chemically, as the sample passes by, much like boulders in a stream. This may be used for both of the above-mentioned reaction formats. These principles are well-documented in the literature (See for example, U.S. Pat. Nos. 5,141,850, 5,160,701, 5,415,994, 5,451,504, 5,559,041, 5,886,154, 5,925,344, 6,093,804, 6,307,028, 6,913,888, 6,955,917, 7,358,055, 7,361,473, 7,427,490).

The technology involved in these lateral flow assays, provide an accurate, easy to use, rapid diagnostic tool. Additional approaches include using the same format for lateral flow tests and dyeing the solid support with a fluorescent dye, the possibility exists to create a truly quantitative test. If the spectral properties of the dyed microspheres to which the antibodies are conjugated are known, the amount of antibody bound at the capture line can be precisely quantified using a fluorometer. The benefit to this is that these tests could become truly quantitative assay. In addition, by placing multiple lines of capture antibodies on the membrane, each for a different analyte, a single test for more than one analyte may be developed. As an example, this format has been used to create a drugs-of-abuse test panel and Biosite's "Triage" was based also on this format (Bangs L. B. (1997) Immunological Applications of Microspheres. The Latex Course Biosite Company, 11030 Roselle St., San Diego, Calif. 92121).

Lateral flow assay technology is also used in the environmental field, where the format provides a rapid, reliable test that can be performed in the field for anything from water pollution to plant disease. Because these diagnostic tests are often performed in harsh environments, the lateral flow format is ideal. With proper preparation and foil pouching, no refrigeration or special handling is required. It also has use in the field of molecular genetics as a simple format for detecting various genetic markers, and DNA- or RNA-related infectious disease pathogens. The guiding principle behind this type of test, the ability to bind a ligand from solution to a solid support, can be performed on genetic material as well as proteins. Another method that can result in reduced development time is the use of protein-coated microspheres, such as ProActive® Streptavidin coated microspheres. By biotinylating the desired conjugate antibodies and then taking advantage of the strong affinity that biotin has for streptavidin, the antibodies are easily attached to the microspheres. Alternatively, Protein A or Protein G coated microspheres will bind many IgG's at the Fc region, allowing for optimized, directed antibody attachment. In this way, a series of assays can be developed rather quickly, using the same solid support, membrane, housing, etc. The only variable would be the conjugate and capture line antibodies used for each specific test. By combining several of these approaches a low-cost, rapid quantitative diagnostic assay for multiple analytes may be prepared for use in the field. For examples of use and methods of preparing such assays see, inter alia, U.S. Pat. Nos. 4,435,504, 4,594,327, 4,624,929, 4,756,828, 4,757,004, 4,837,395, 4,857,455, 4,911,794, 4,945,205, 4,956,275, 4,999,285, 5,039,607, 5,075,078, 5,087,556, 5,089,383, 5,164,294, 5,234,813, 5,248,619, 5,252,293, 5,998,221, 5,939,331, 5,908,757, 5,624,809, 5,529,752, 5,468,647, 5,451,507, 5,435,970, 5,334,513, 6,194,220, 6,277,646, 6,686,167, 6,855,561, 6,969,591, 7,067,264, 7,179,657 and 7,226,793; and published U.S. patent application nos.: 20080160549, 20070281370, 20070190531, 20070111323, 20060160084, 20040068101, 20040058395, 20030211634, 20030157699, 20030100128, 20030049167, 20030027222, 20020106696 and 20020085958, among others.

An immunochromatographic assay, or lateral flow test for the level of p1978 in a sample of a patients bodily fluid, such as saliva, would be very useful in some embodiments of the testing methods described herein, as it provides several potential benefits. For example, in some applications, it may be used in a kit designed to facilitate the process of identifying individuals at increased risk for breast cancer in rural areas or even in a physician, dentist or veterinarian's office or public clinic. In some embodiments such an assay need be only semi-quantitative as only those samples whose cytochrome p450 are decreased or ubiquitin levels are increased above the normal range need be detected. As an immunoassay, this test could be titrated to obtain the desired cutoff and sensitivity.

Nephelometry is a technique performed by shining light on a sample, and measuring the amount of light scattered. This technique is widely used in clinical laboratories because it is relatively easily automated. It is based on the principle that a dilute suspension of small particles will scatter light (often but not necessarily a laser) passed through it rather than simply absorbing it. The amount of scatter is determined by collecting the light at an angle (usually at about 70 or 75 degrees). Such immunoturbidimetric assays (protein immunoassays) are read using a Photometer (such as a DTN-410, DIALAB GmbH, Germany) or autolyzer Photometer (DTN-410K, DIALAB GmbH). Antibody and the antigen are mixed in concentrations such that only small aggregates are formed that do not quickly settle to the bottom. The amount of light scatter is measured and compared to the amount of scatter from known mixtures. The amount of the unknown is determined from a standard curve.

Enzyme multiplied immunoassay technique, or EMIT, is a common method for screening urine and blood for drugs, both legal and illicit. First introduced by Syva Company in 1973, it is the first homogeneous immunoassay to be widely used commercially. A mix and read protocol has been developed that is exceptionally simple and rapid. The most widely used applications for EMIT are for therapeutic drug monitoring (serum) and as a primary screen for abused drugs and their metabolites (urine). Early patents covering the major aspects of the method are U.S. Pat. Nos. 3,817,837 and 3,875,011. While still sold by Siemens Healthcare under its original trade name, EMIT, assay kits with different names that employ the same technology are supplied by other companies. The method is highly reliable and reliance on its results has even been upheld by the US Supreme Court. Older ELISAs utilize chromogenic substrates, while many of the newer assays employ fluorogenic substrates enabling increased sensitivity, both types can be read on an ELISA microplate reader (such as the DIAREADER:DIALAB GmbH, Germany) of the appropriate measuring range, for example from 400 nm n to 750 nm.

Additionally, analytical scale immunoprecipitations can also be used to detect the presence of an analyte, such as p1978 in bodily fluids, preferably saliva. Monodispersed magnetic beads are also available as a support material which offers certain advantages over polydisperse agarose beads. Magnetic beads have the ability to bind extremely large protein complexes and the complete lack of an upper size limit for such complexes, as unlike agarose beads which are sponge-like porous particles of variable size, magnetic beads are small, solid and (in the case of monodisperse magnetic beads) spherical and uniform in size. The lower overall binding capacity of magnetic beads for immunoprecipitation make it much easier to match the quantity of antibody needed for diagnostic immunoprecipitations precisely with the total available binding capacity on the beads which results in decreased background and fewer false positives. The increased reaction speed of the immunoprecipitations using magnetic bead technologies results in superior results when the analyte protein is labile due to the reduction in protocol times and sample handling requirements which reduces physical stresses on the samples and reduces the time that the sample is exposed to potentially damaging proteases. Agarose bead-based immuno-precipitations may also be performed more quickly using small spin columns to contain the agarose resin and quickly remove unbound sample or wash solution with a brief centrifugation (Celis, J. E., Lauridsen, J. B., and Basse, B. (1994) Determination of antibody specificity by Western blotting and immunoprecipitation. In: Celis, J. E. (ed.), CELL BIOLOGY. A LABORATORY HANDBOOK, Academic Press, New York, Vol. 2, pp. 305-313. Mason, D. W., and Williams, A. F. (1986) Kinetics of antibody reactions and the analysis of cell surface antigens. In: Weir, D. M., Herzenberg, L. A., Blackwell, C., and Herzenberg, L. A. (ed.), HANDBOOK OF EXPERIMENTAL IMMUNOLOGY, Blackwell, Oxford, vol. 1, chapter 38.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Experimental design: The experimental design (see FIG. 1) was to seed the HCC38 breast cancer cell line (BCCL) with the p1978 pep-tide in order to determine the effects of the peptide on cell growth. The HCC38 cell line was chosen because of its triple negative receptor status. Triple negative tumors generally do not respond to receptor-targeted treatments and can be particularly aggressive. They are more likely to recur than other subtypes of breast cancer.

Figure 1:
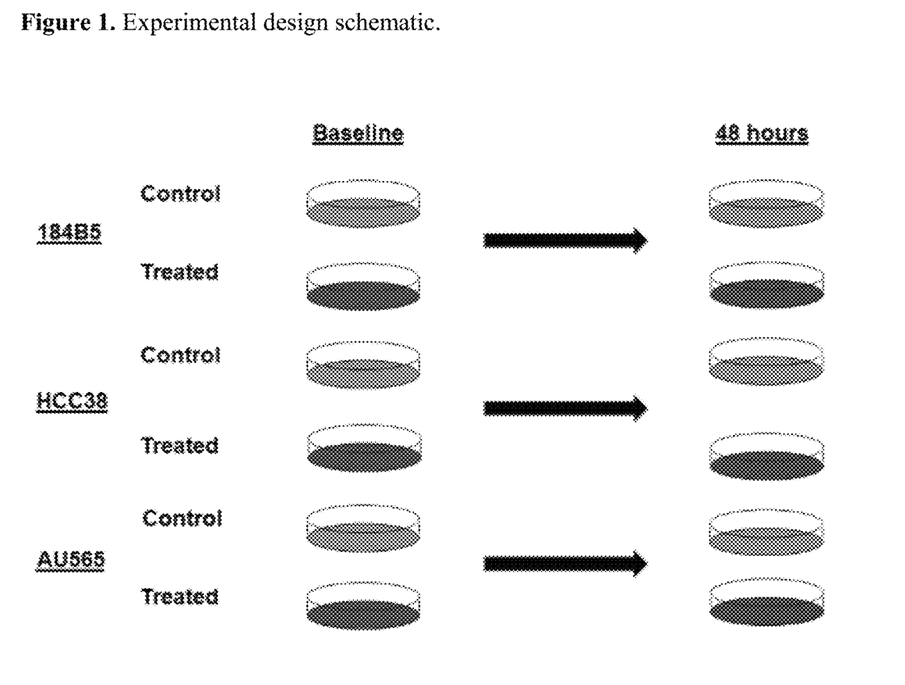
FIG. 1: Experimental design schematic.

The 184B5 (normal breast tissue cells) were seeded to serve as a negative control while the AU565 BCCL, a cell line with a positive Her2/neu and p53 receptor status, was inoculated to serve as a positive control. In the initial phase, treatment cell lines were treated with 8.26 µg/ml of p1978. The con-centration corresponds closely to the average SMR3B (the parent protein of the p1978 peptide), concentration, plus one standard deviation found in healthy breast tissues. A second experiment was performed doubling the concentration of 1978 to 16.52 µg/ml. FIG. 1 represents a schematic of the design used for the study.

As shown in FIG. 1, seeding with p1978 for both experiments was initiated at 30% confluence in the culture medium at 0.1×FBS (fetal bovine serum). Corresponding unseeded cell lines served as controls. The controls were treated with a placebo containing 1.0 ml of sterile PBS (for cell culture). An expanded dose-response experiment was not performed due to limited resources. The experiment ended 48 hours after seeding. The outcome variables of this study were total cell count, live cell count and percent viability.

Peptide synthesis: In a previous proteomic studies, LC-MS/MS analysis of saliva the proline rich protein SMR3B (P02814) was found to be up-regulated in saliva secondary to carcinoma of the breast in situ. The proline rich peptide PRGPYPPGPLAPPQ (p19'78; SEQ ID NO: 1) was the most abundant peptide segment in identifying the total protein SMR3B. The total coverage of the SMR3B (MKSLTWILGL[10] WALAACFTPG[20] ESQRGPRGPY[30] PPGPLAPPQP[40] FGPGFVPPPP[50] PPPYGPGRIP[60] PPP-PAPYGPG[70] IFPPPPPQP (SEQ ID NO: 4)) was 67% with p1978 being involved with 76% of the polypeptide coverage.

New England Peptide™ (Gardner, M A) synthesized peptide p1978 using their proprietary technology. Purity was determined by HPLC and was to be greater than 85%. The peptide was supplied as a lyophilized powder and required reconstitution.

Cell lines: Human breast cell lines HCC38 (HCC38 BL (ATCC® CRL-2346™), AU565 (ATCC® CRL2351™) and 184B5 (ATCC® CRL-8799™) were purchased from the American Type Culture Collection. Cell line descriptions are summarized in Table 1.

TABLE 1

Cell types with receptor status.

| Cell Line | Disease | Cell Type | Receptors |
|---|---|---|---|
| 184B5 | Normal | Chemically transformed | N/A |
| HCC38 | Adenocarcinoma | Stage IIB tumor | ER$^-$, PR$^-$, Her2$^-$ |
| AU565 | Adenocarcinoma | Pleural effusion | Her2$^+$, Her3$^+$, Her4$^+$, p53$^+$ |

Cell growth procedures: The aforementioned cell lines were thawed in a 37.0 water bath with gentle agitation. The vials were decontaminated and the cells were added drop wise to 9 ml of their prospective culture media while gently mixing. The cell suspension was centrifuged at 1,000 rpm for five minutes. The supernatant was carefully removed and the cell pellet was resuspended in 5.0 ml of media. Each cell line was checked for viability using a hemocytometer and a cell count/ml was calculated. Nine plates were seeded of each cell line at a total of 1.0×106 cells/100 mm plates. Once the plates reached 30% confluency, nine plates of each cell line were treated with 8.26 µg/ml (4.95 µM) of p1978 peptide and a set of nine control plates were treated with 1.0 ml of phosphate buffered saline (PBS). They were incubated and harvested by trypsinization in 48 hours. The cells from each plate were counted for the total number of cells and were assessed for viability using the trypan blue exclusion test of cell viability. The same procedures were repeated for the higher 16.52 ug/ml (9.88 uM) dose.

Statistics: Data was tabulated using SPSS statistical software. The outcome variables of this study were total cell count, live cell count and percent viability. To assess these variables, descriptive statistics were employed to compare p1978 treated cells relative to the control cells. The approach consisted mainly of bar charts, mean cell counts and mean percentages. The cellular growth rate was determined by subtracting the resultant or final cell count from its baseline value. The difference was divided by 48 hours the growing time for the cells. The results were expressed in cells/hour.

A homoscedastic univariate t-test was computed for differences between the treated and the control groups. The arithmetic mean value of the control group was used as the "cut-point" value. The alpha level was p<0.05.

Figure 2:
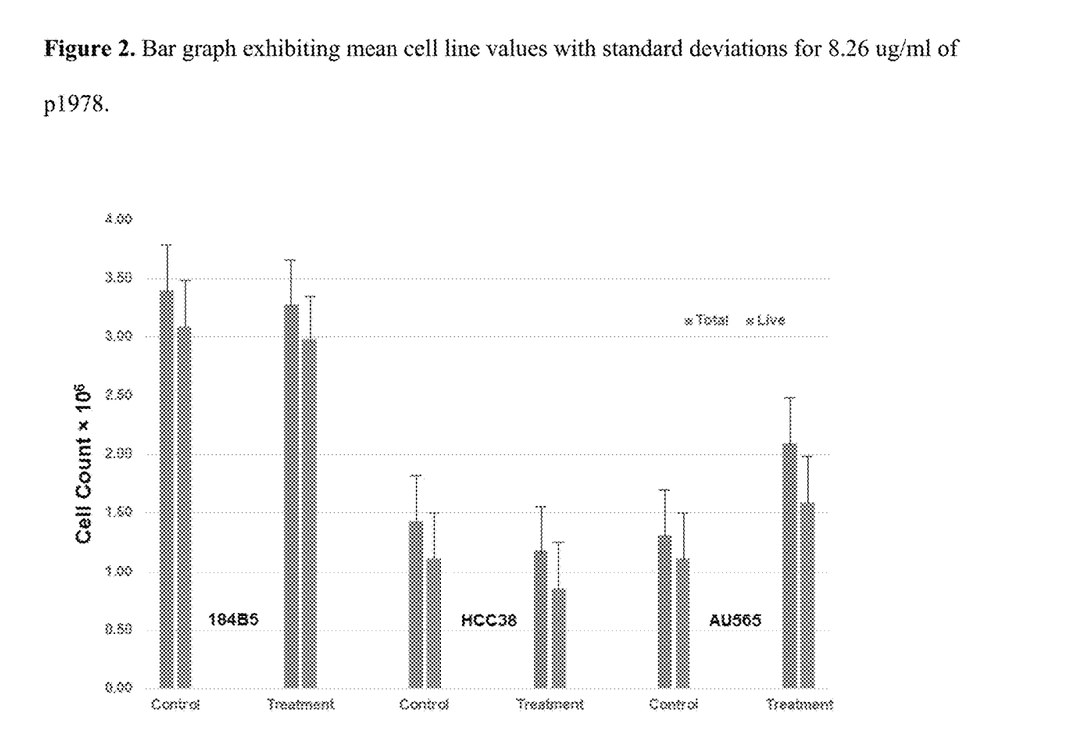
FIG. 2: Bar graph exhibiting mean cell line values with standard deviations for 8.26 ug/ml of p1978.

Dosing cell lines with 8.26 ug/ml of p1978: The results of this experiment are illustrated in FIG. 2. The 184B5 cell line (normal breast tissue) exhibited slightly higher cell counts for the treated cells for both total (7.5%) and living cell counts (3.5%) as compared to the control. The addition of the peptide produced an almost negligible difference in growth rate between the treated and the controls.

Unlike the 184B5 cell line, the HCC38 cell line produced a 20.8% and a 33.2% reduction for both total and living cell counts respectively. Both cell counts exhibited a similar knock down trend; however, the living cell count was nearly significant from the control at t=−3.25 and a p value of 0.08. While not statistically significant, it may be clinically relevant. Treated HCC38 growth rate is over lower than control HCC38 growth rate (Table 3). The AU565 cell line percent viability was lower for the treated AU565 as compared to the control (61% vs. 80%). The total (31.5%) and live (11.7%) cell count values in the treated AU565 line were higher than AU565 control group.

Dosing cell lines with 16.52 ug/ml of p1978: The results of this experiment are illustrated in Table 2 and FIG. 3. As illustrated in Table 2 and FIG. 3, there was an increase in the total (22.4%) and living (63.7%) cell counts for the treated 184B5 cells as compared to the control. There was no effect, however, on cell viability or growth rate (Table 3).

TABLE 2

Mean cell line values with standard deviations for 16.52 µg/ml dose of p1978

| Cell line | Status | Total × $10^6$ | Live × $10^6$ | % Live |
|---|---|---|---|---|
| 184B5 | Baseline | 2.29 | 2.25 | 98% |
|  | Control | 4.01 (±1.06) | 3.82 (±0.99) | 95% |
|  | Treated | 4.91 (±0.63) | 4.82 (±0.75) | 98% |
|  | Control - Baseline | 1.72 | 1.57 | — |
|  | Treated - Baseline | 2.62 | 2.57 | — |
|  | Treated - Control | 0.90 | 1.00 | — |
| HCC38 | Baseline | 1.00 | 0.77 | 77% |
|  | Control | 2.64 (±0.75) | 2.54 (±0.69) | 96% |
|  | Treated | 2.03 (±0.62) | 1.87 (±0.43) | 92% |
|  | Control - Baseline | 1.64 | 1.77 | — |
|  | Treated - Baseline | 1.03 | 1.10 | — |
|  | Treated - Control | −0.61 | −0.67 | — |
| AU565 | Baseline | 1.90 | 1.36 | 72% |
|  | Control | 1.87 (±0.56) | 1.30 (±0.44) | 70% |
|  | Treated | 2.14 (±0.50) | 1.60 (±0.42) | 75% |
|  | Control - Baseline | −0.03* | −0.06* | — |
|  | Treated - Baseline | 0.24* | 0.24* | — |
|  | Treated - Control | 0.27 | 0.30 | — |

Note.
*represents $10^5$.

Figure 3:
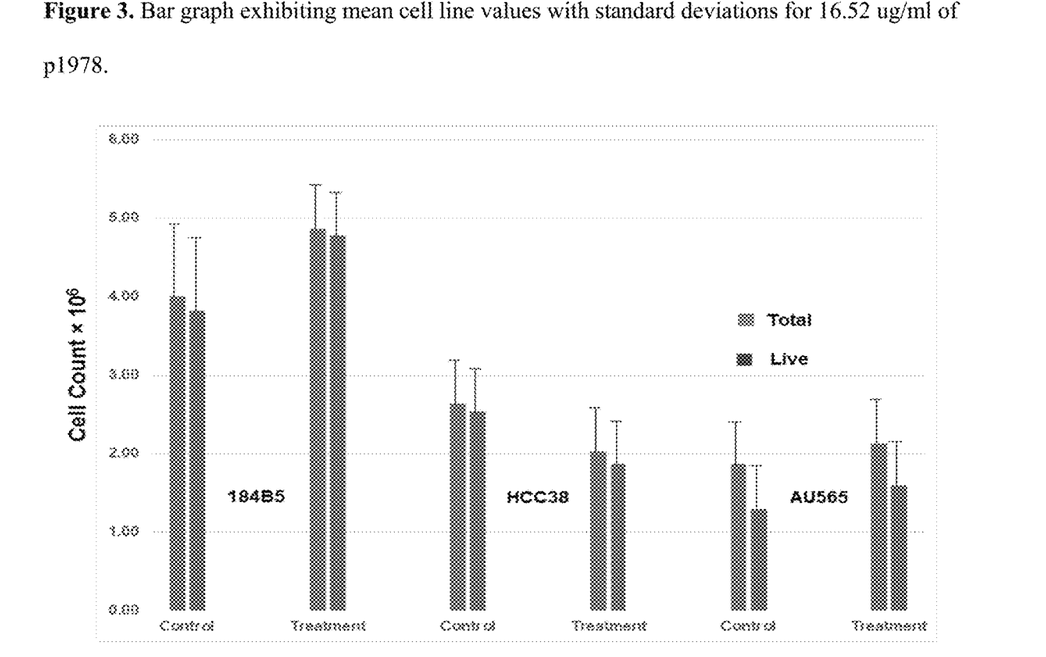
FIG. 3: Bar graph exhibiting mean cell line values with standard deviations for 16.52 ug/ml of p1978.

With respect to the HCC38 cell line, the average total number of cells were higher in then control (22.4%) than in treated HCC38 cell line indicating a knockdown effect on HCC38 cell line. Likewise, there was a 37.9% decrease in the number of living cells in the seeded HCC38 cell line as compared to the control. This was statistically significant (t=−3.08; p<0.05). As shown in Table 3, the HCC38 treated group had a lower growth rate than control (−38% difference).

The average total cells were lower in control than in treated AU565 cell line. No knockdown effect was observed among the AU565 cell lines as observed in the in the HCC38 cell line. Additionally, there was an effect on the percent viability as it indicated a 23.1% increase in living cell count. The AU565 treated group also exhibited a growth rate higher than the control (Table 3).

TABLE 3

Growth rates for cell lines expressed as cells/hour

|  | Cell line | Status | Total growth rate* | Live growth rate* |
|---|---|---|---|---|
| Dosing cell lines with 8.26 μg/ml of p1978 | 184B5 | Control | 1.36 | 0.81 |
|  |  | Treated | 1.11 | 0.59 |
|  | HCC38 | Control | 0.60 | 0.29 |
|  |  | Treated | N.G. | N.G. |
|  | AU565 | Control | N.G. | N.G. |
|  |  | Treated | 1.38 | 0.77 |
| Dosing cell lines with 16.52 μg/ml of p1978 | 184B5 | Control | 4.56 | 3.28 |
|  |  | Treated | 7.83 | 2.77 |
|  | HCC38 | Control | 3.42 | 3.69 |
|  |  | Treated | 2.16 | 2.29 |
|  |  | Control | N.G. | N.G. |
|  | AU565 | Treated | 0.50 | 0.50 |

Note.
*represents $10^4$;
N.G. = Negative Growth.

Without further elaboration, it is believed that one skilled in the art can, using the description herein, utilize the present methods to its fullest extent. The embodiments described herein are to be construed as illustrative and not as constraining the remainder of the disclosure in any way whatsoever. While preferred embodiments have been shown and described, many variations and modifications thereof can be made by one skilled in the art without departing from the spirit and teachings of the presently disclosed methods. Accordingly, the scope of protection is not limited by the description set out above, but is only limited by the claims, including all equivalents of the subject matter of the claims. The disclosures of all patents, patent applications and publications cited herein are hereby incorporated herein by reference, to the extent that they are consistent with the present disclosure set forth herein.

REFERENCES

[1] Kiberstis P, Roberts, L. A race still unfinished. Science 2014; 343:1451.
[2] Servick K. Breast cancer: a world of difference. Science 2014; 343:1452-1453.
[3] Lebrecht A, Boehm D, Schmidt M, et al. Diagnosis of breast cancer by tear proteomic pattern. Cancer Genomics Proteomics 2009; 6:177-182.
[4] Eccles, S A, et al. Clinical research gaps and translational priorities for the successful prevention and treatment of breast cancer. Breast Cancer Res 2013; R92.
[5] Koffler J, Holzinger D, Sanhueza G A, et al. Submaxillary gland androgen-regulated protein 3A expression is an unfavorable risk factor for the survival of oropharyngeal squamous cell carcinoma patients after surgery. Eur Arch Otorhinolaryngol 2013; 270(4):1493-1500.
[6] Streckfus C, Bigler L. A catalogue of altered salivary proteins secondary to invasive ductal carcinoma: a novel in vivo paradigm to assess breast cancer progression. Scientific Reports 2016; 30800(6):1-18
[7] Neve R M, Chin K, Fridlyand J, et al. A collection of breast cancer cell lines for the study of functionally distinct cancer subtypes. Cancer Cell 2006; 10(6):515-527.
[8] Radicioni G, Stringaro A, Molinari A, et al. Characterization of the cell penetrating properties of a human salivary proline-rich peptide. Biochimica et Biophysica Acta 2015; 1848:2868-2877.
[9] Schlessinger J. SH2/SH3 signaling proteins. Curr Opin Genet Dev 1994; 4(1):25-30.
[10] Kay B K, Williamson M P, Sudol M. The importance of being proline: the interaction of proline-rich motifs in signaling proteins with their cognate domains. FASEB J 2000; 14:231-241.
[11] Lemmon M A, Ladbury J E, Mandiyan V, et al. Independent binding of peptide ligands to the SH2 and SH3 domains of Grb2. J Biol Chem 1994; 269(50):31653-31658.
[12] Mayer B J, Baltimore D. PSignaling through SH2 and SH3 domains. Trends Cell Biol 1993; 3:8-13.
[13] Delbruck M. Chapter 6: Cytoplasmic signaling circuitry programs many of the traits of cancer. In: The Biology of Cancer. Weinberg R (edit), New York & London: Garland Sciences, Taylor & Francis Group, L L C., 2014, pps. 184-190.
[14] Palmerini C A, Mazzoni M, Radicioni G, et al. Antagonistic Effect of a Salivary Proline-Rich Peptide on the Cytosolic Ca2+ Mobilization Induced by Progesterone in Oral Squamous Cancer Cells. PLoS One 2016; 11(1): e0147925. PMID: 26814504 http://dx.doi.org/10.1371/journal.pone.0147925. PubMed: 26814504
[15] Boonyaratanakornkit V, Scott M P, Ribon V, et al. Progesterone receptor contains a proline-rich motif that directly interacts with SH3 domains and activates c-Src family tyrosine kinases. Mol Cell 2001; 8(2):269-280.
[16] Hashimoto S, Hirose M, Hashimoto A, et al. Targeting AMAP1 and cortactin binding bearing an atypical src homology 3/proline interface for prevention of breast cancer invasion and metastasis. Proc Natl Acad Sci USA 2006; 103(18):7036-7041.
[17] Zhang J, Wong H, Ramanan S, et al. The proline-rich acidic protein is epigenetically regulated and inhibits growth of cancer cell lines. Cancer Res. 2003; 63(20): 6658-6665.

What is claimed is:

1. A method of treating or preventing a cancer in a subject comprising administering an effective amount of a composition comprising a recombinant polypeptide comprising the amino acid sequence of p1978 (SEQ ID NO: 1).

2. The method of claim 1, wherein the cancer is a breast cancer.

3. The method of claim 2, wherein the breast cancer is triple negative breast cancer.

4. The method of claim 1, wherein the composition is administered by intravenous injection or catheter delivery.

5. The method of claim 2, wherein the composition is administered by intravenous injection or catheter delivery.

6. The method of claim 3, wherein the composition is administered by intravenous injection or catheter delivery.

7. The method of claim 1, wherein the recombinant polypeptide is a fusion protein comprising the amino acid sequence of p1978 (SEQ ID NO: 1) and a heterologous polypeptide sequence.

8. The method of claim 1, wherein the recombinant polypeptide is no more than 50 amino acids in length.

9. The method of claim 1, wherein the recombinant polypeptide is no more than 20 amino acids in length.

10. The method of claim 1, wherein the N-terminus, the C-terminus or both are blocked.

* * * * *